United States Patent [19]
Hildenbrand et al.

[11] Patent Number: 5,160,436
[45] Date of Patent: Nov. 3, 1992

[54] ASYMMETRIC SANDWICH MEMBRANE SYSTEM HAVING REDUCED ASCORBATE INTERFERENCE

[75] Inventors: Karlheinz Hildenbrand, Krefeld; Herbert Hugl, Gladbach; Rolf Dhein, Krefeld, all of Fed. Rep. of Germany

[73] Assignee: Miles Inc., Elkhart, Ind.

[21] Appl. No.: 693,379

[22] Filed: Apr. 30, 1991

[30] Foreign Application Priority Data

May 11, 1990 [DE] Fed. Rep. of Germany ....... 4015157

[51] Int. Cl.$^5$ .............................................. B01D 69/00
[52] U.S. Cl. ..................................... 210/638; 210/641; 210/490; 422/56
[58] Field of Search ................. 435/182, 288; 422/56; 210/314, 335, 486, 487, 489, 490, 500.43, 638, 641

[56] References Cited

U.S. PATENT DOCUMENTS

| | | | |
|---|---|---|---|
| 3,966,439 | 6/1976 | Vennos | 210/314 X |
| 4,169,014 | 9/1979 | Goldberg | 435/182 |
| 4,774,192 | 9/1988 | Terminiello et al. | 422/56 X |
| 4,824,639 | 4/1989 | Hildenbrand et al. | 422/56 |
| 5,039,421 | 8/1991 | Linder et al. | 210/500.43 X |

*Primary Examiner*—Frank Spear
*Attorney, Agent, or Firm*—Jerome L. Jeffers

[57] ABSTRACT

Disclosed is a diagnostic test device which comprises a fluid permeable structural support member having on one side thereof a layer of a macroporous membrane comprising polyethyleneimine impregnated with iodate ion and on the other side of the support member having a layer of a microporous membrane having dispersed therein a chromogenic indicator capable of providing a colored response upon being oxidized.

The intensity of the colored response is less subject to ascorbate interference due to the activity of the iodate ion.

6 Claims, No Drawings

ASYMMETRIC SANDWICH MEMBRANE SYSTEM HAVING REDUCED ASCORBATE INTERFERENCE

BACKGROUND OF THE INVENTION

In the context of clinical chemical analysis methods, diagnosis test strips have gained more and more importance in recent years. The developments of recent years concentrate, above all, on the following aims:

1) improving the accuracy and reliability so that results of the quality of conventional wet chemical methods can be achieved. It was possible here to achieve enormous advances using plastic matrices, which can be produced with high uniformity, in combination with reflectometric analysis methods.
2) expanding the test range from glucose to other analytes in blood and urine including immunodiagnostic detection reactions, and
3) a test procedure which is as straightforward as possible, which in the ideal case is restricted only to sample application. Handling-independent test systems of this type, frequently also called technique-independent in English usage, are an important advantage compared with the conventional wipe-off test strips, especially for self-diagnosis by untrained patients.

To achieve the property profiles mentioned, a number of demands are made, in particular, on the matrix system of the dry chemical detection elements. Thus, in blood diagnosis tests in which the wiping-off of the excess of sample should be avoided, the removal of red blood cells must take place within the reagent matrix. The serum should diffuse into a further reagent layer and generate a color reaction with specific detection reagents there which is unaffected by erythrocytes.

In many cases, it is convenient or even necessary to embed the reagents needed for the detection spatially in separate layers. For example, in German Auslegeschrift 1,598,153, systems are described in which a permeable layer in the form of a plastic gauze, which, for example, can remove interfering ascorbic acid in a selective reaction, is connected to the reagent layer. The separate embedding of the detection reagents in different matrix layers is frequently of great advantage, in particular in complicated detection reactions which proceed in reaction cascades and require enzyme systems having different optimum pH ranges. In immunodiagnostic detection reactions, moreover, matrix layers which enable immobilization of antigens, antibodies, enzymes or other biological active substances, are additionally necessary.

Several developments have already been described for the preparation of detection systems of this type, which as a rule are based on a multilayer matrix structure. Thus, European Patent application 0,267,519 describes test carriers which essentially consist of glass fiber wadding for erythrocyte removal and a reagent layer composed of a microporous polymer film. However, the total system still requires a number of other auxiliary layers, so that for the total structure, depending on the detection reaction, seven or more individual layers are combined in a relatively complicated structure.

In addition to complicated production processes, the demands on precision are increasingly difficult to fulfill with an increasing number of individual layers fixed to one another.

German Patent Specification 3,922,495 describes diagnosis systems based on asymmetric membrane matrices which enable a plasma separation within the membrane layer and thus no longer have to be wiped off. For complicated detection reactions or with regard to an improved distribution of the sample on the application side, additional layers, such as special papers or waddings are also fixed there above the actual reagent matrix.

Multilayer integral analytical elements, in particular those based on gelatin films, have already been known for a relatively long time. Thus a typical diagnosis system as described in U.S. Pat. No. 3,922,158 consists, for example, of individual layers for carrier, reagent layer, reflection layer, filter layer and spreading layer. The preparation of multilayer gelatin films is best known from photography and presents no difficulties in terms of production technique. Further processing to give the diagnosis system also proceeds simply, since the multilayer systems can be handled as a film and several layers do not have to be laminated or glued one above the other in complicated processes as in the above-mentioned systems. However, a disadvantage of gelatin systems is that they are non-porous, swelling layers, so the physiochemical processes which are strongly temperature-dependent also occur in addition to the desired detection reaction during sample application.

For this reason, the gelatin systems mentioned only work accurately and reproducibly under thermostated conditions. The gelatin systems mentioned can thus only be employed in large-scale clinical equipment where the maintenance of defined temperature and moisture conditions is possible.

Multilayer, microporous membrane systems which are entirely integrated in one film are accordingly of particular interest for the future generation of diagnosis systems. The complicated laminating to one another of different layers would as a result become unnecessary. Systems of this type would combine the excellent properties of non-swelling polymer membranes which are adjustable with respect to porosity and chemical composition with the ability for simple further processing of multilayer gelatin films.

SUMMARY OF THE INVENTION

The present invention is a diagnostic test device which comprises a fluid permeable structural support member having a macroporous membrane on one side and a microporous membrane on the other side thereof. When a fluid sample to be analyzed is applied to the macroporous membrane, there is permitted free flow of fluid through this membrane and the support member into the microporous membrane. By use of this configuration it is possible to separate incompatable reagents in a unitary test device and yet provide a quick and accurate means for determination of an analyte such as glucose in the fluid specimen being tested. For example, in a test for glucose, the enzymes which react specifically with glucose can be included in the macroporous membrane with the chromogenic indicator in the microporous membrane. In a similar manner, reagents for the elimination of substances which interfere with the colormetric assay, such as ascorbate in a test for hemoglobin, can be placed in the macroporous layer where they will not come into contact with the chromogen.

DESCRIPTION OF THE INVENTION

It has surprisingly been found that certain membranes adhering to polymer fabrics or a non-woven support member are suitable for the preparation of double membranes having a sandwich-like structure. In these double membranes, two different membranes are in each case situated on opposite sides of a polymeric fabric or nonwoven carrier material.

The sandwich-like structure is formed such that a macroporous membrane having a pronounced absorption behaviour and which is used as the application side during the detection reaction is situated on one side of the fabric carrier material.

The polymer membrane adhering to the other side of the fabric is used as the reagent layer and is preferably microporous. The macroporous membrane will preferably have a pore size greater than $0.2\mu$, typically up to $20\mu$, in diameter and the microporous membrane in this connection is to be understood as having a pore diameter of about 0.2 $\mu$m or less.

Membranes having an asymmetric structure, for example Dralon membranes, such as are described in German Patent Specification 3,922,495, are preferably employed as the microporous reagent layer. The particular advantage of these membranes is the possibility of erythrocyte removal within the membrane layer during sample application to the back of the membrane.

The application and reagent side of the sandwich membrane can also differ in the chemical structure of the reagent matrix in addition to the porosity. Thus, it is possible, as the examples show, to combine a macroporous application layer which contains free amino groups with a microporous reagent layer which contains free carboxyl groups. In sandwich membranes of this type, oxidants for selectively destroying ascorbic acid, which are immobilized by ionic bonding, can be introduced into the amino group-containing macroporous application layer by impregnating with aqueous iodic or periodic acid. The free carboxyl groups of the reagent layer, on the other hand, are advantageous for the stabilization of the enzymatic reagent system and the reaction color formed. Owing to the ionic immobilization in combination with the sandwich-like matrix structure, it is also possible, surprisingly, to employ periodates for selectively destroying ascorbic acid, although according to German Offenlegungsschrift 3,012,368 it should not be possible because of their oxidation potential to employ these in combination with indicators such as 3,3′,5,5′-tetramethylbenzidine.

The detection reagents are incorporated, as described in German Offenlegungsschrift 3,497,359, either by stirring into the casting solution (in the case of water-insoluble reagents), by subsequent impregnation or by a combination of these two methods. In this connection, the extruder method described in U.S. Pat. No. 4,837,043 is preferably used for impregnating and enables the separate incorporation of different reagents in the front and back of the sandwich membrane.

Contrary to initial ideas and current knowledge, the preparation of membranes having a sandwich-like structure is by no means trivial. Thus, in first attempts, commercial ultrafiltration membranes, for example polysulphone membranes, coated on the support member side with a polymer casting solution of polyacrylonitrile and coagulated in a water bath were employed. In parallel attempts, the same casting solution was coated onto polymer wadding i.e., a non-woven support structure, as a carrier material, and onto non-porous polymer films which have been described, for example in German Offenlegungsschrift 3,407,359, as carriers for diagnosis test strips. While it was possible to obtain defect-free membranes in both parallel examples, which do not lead to sandwich membranes, the coating on the wadding side of the ultrafiltration membranes gave very defective membranes which were completely unusable for the desired intended use.

In other attempts, the Dralon matrices which adhere to polymer fabrics, developed with reference to diagnosis matrices in German Patent Specification 3,922,495, were employed. Here too, the fabric side of the Dralon membranes was coated with a polymer casting solution and coagulated with reference to membranes having a sandwich-like structure. In analogy to the above-mentioned coatings on ultrafiltration membranes, here too membrane layers having a multiplicity of defects were obtained. The defects in the newly formed membranes as a rule indicated included air bubbles.

Surprisingly, the production of the sandwich membranes is achieved without problems by employing macroporous membranes adhering to polymer fabrics for coating, such as are described in German Patent Specification 3,809,523. In this process, casting solutions of Dralon ® polymers (polyacrylonitrile), such as are described in German Patent Specification 3,922,495, are coated onto the fabric side of the macroporous polymer blend membranes described in German Patent Specification 3,809,523 and coagulated. After drying, membrane matrices having a sandwich-like structure were obtained, the macroporous polymer blend membrane being on one side and the microporous asymmetric Dralon ® membrane being on the other side of the fabric material.

In other attempts, it was found that microfiltration membranes, for example Biodyne ® membranes from Messrs. Pall are suitable for coating with a second membrane. The nylon Biodyne ® membrane here assumed the function of the above-mentioned macroporous polymer blend membranes (application side).

To evaluate the efficiency, the detection system for glucose (glucose oxidase, peroxidase, 3,3′,5,5′-tetramethylbenzidine=TMB) was incorporated into the sandwich-like diagnosis matrices according to the invention and they were tested with whole blood. As the examples illustrate in more detail, a macroporous polymer blend membrane of polyester fabric was first prepared in analogy to German Patent Specification 3,809,523, and after drying, was coated with a TMB-containing polyacrylonitrile (Dralon ®) formulation in accordance with pending U.S. patent application Ser. No. 539,436, coagulated and dried. An impregnation solution of glucose oxidase and peroxidase was then coated onto the surface of the microporous Dralon ® membrane and dried.

The membrane was tested with whole blood and with aqueous glucose solutions of increasing glucose contents. A corresponding single-layer Dralon ® membrane prepared in accordance with German Patent Specification 3,922,495 was used for comparison. The test results showed the particular advantages of the test system having the sandwich-like structure. While, after application of blood to the opposite side, it was possible in both cases to observe a color reaction which was unaffected by erythrocytes, the uniform distribution of the blood sample on the application side and the problem of the overlying sample excess turned out to be substantially more favorable in the case of the sandwich membranes. It was also possible to achieve a more favorable result with the ability to differentiate color in the case of the sandwich systems.

The advantage turned out to be even more significant with reference to an example having a connected reaction, where, as already mentioned, selective protection of ascorbic acid in the glucose test was used as an example. As the following examples show, significantly more effective protection of ascorbic acid than in single layer matrices can be achieved by the ascorbic acid anti-oxidants immobilized in the application layer.

In the course of further investigations, it was surprisingly found that the polyethyleneimine-containing macroporous membrane layers mentioned immobilize enzymes with a surprisingly high binding strength. This was found by comparison of the following experiments: a sandwich membrane, having a macroporous polyethyleneimine-containing membrane as an application layer and a TMB-containing microporous Dralon membrane as a reagent layer, was coated on the reagent layer side with an enzyme impregnation solution of glucose oxidase and peroxidase with the aid of a hand doctor blade and dried. In a parallel example, the enzyme coating was carried out on the macroporous application layer side.

The diagnosis systems were tested with water or buffer solution containing glucose solutions directly and after a washing-out attempt. While the unrinsed specimen in both cases showed good reactivities, it was only possible to find unchanged reactivity after rinsing in the case of the sandwich membrane.

In this case, not the specific, sandwich-like membrane structure, but, as the other experiments showed, the structure of the macroporous polymer blend membranes described in German Patent Specification 3,809,523 is responsible for the enzyme immobilization, it being possible by adding polymers having ion exchanger ability, for example polyethyleneimine for free amino groups or polyacrylic acid for free carboxylate groups, to increase the binding strength further.

The following examples are used for the further illustration of the multilayer matrix systems according to the present invention.

EXAMPLE 1

Preparing a sandwich membrane from a macroporous polymer blend layer and a microporous polyacrylonitrile membrane.

a) Macroporous polymer blend membrane

A polymer blend casting solution was prepared from the following components:

| | |
|---|---|
| Polyacrylonitrile (Dralon T ®, Bayer AG) | 9.55 g |
| Polyurethane (Desmopan KBH, Bayer AG) | 34.01 g |
| Polyvinyl acetate (Mowilith 50, Hoechst AG) | 56.44 g |
| Talc AT 1 (Norwegian talc) | 193.53 g |
| Dimethyl sulphoxide (DMSO) | 592.17 g |
| Pluronic L 62 (polypropylene oxide, BASF, Wyandotte) | 3.91 g |

The casting solution was prepared with the aid of a high-speed dissolver. It was filtered through a 25 μm sieve and degassed in vacuo.

The casting solution was coated on a polyester fabric (PES 1973, Messrs. Verseidag, Krefeld) with the aid of a doctor blade using a wet coating of 250 μm, then coagulated in water and dried in warm air.

German Patent Specification 3,809,523 give information about the chemical structures of the polymers employed.

b) Microporous polyacrylonitrile membrane

A casting solution was prepared from the following components with the aid of a high-speed dissolver:

| | |
|---|---|
| Dralon N ® (anionically modified polyacrylonitrile, Bayer AG) | 100.0 g |
| Dimethyl sulphoxide (DMSO) | 596.3 g |
| Barium sulphate (Blanc fixe mikron, Messrs, Sachtleben) | 156.4 g |
| 3,3',5,5'-tetramethylbenzidine (TMB) | 8.4 g |

After filtration and degassing, the solution was applied in a wet layer thickness of 150 μm to the fabric side of the macroporous membrane prepared in a) and coagulated in water. The membrane with the sandwich-like structure was obtained after drying.

To test the properties as a diagnosis system, the microporous Dralon side of the membrane was coated with an enzyme impregnating solution of the following composition using a wet coating of 100 μm and dried:

| | |
|---|---|
| 119 mg of glucose oxidase | (180 U/mg) |
| 335 mg of peroxidase | (149 U/mg) |
| 500 mg of Triton × 100 | |

Citrate buffer (pH 5.5, 0.2 ml) up to the calibration mark of 50 ml. Test with whole blood and aqueous glucose solutions (50, 100, 250, 400 and 600 mg/dl):

A few seconds after application of blood to the macroporous membrane layer, it was possible to observe a color reaction which was unaffected by erythrocytes on the opposite side.

The applied blood (10 μl) was distributed spontaneously and uniformly on the 0.5×0.5 cm test field and was largely absorbed into the reagent matrix after about 10 seconds.

Corresponding to the concentration, blue colorations of increasing color intensity which enabled a good differentiation ability resulted with the aqueous standard solutions.

In the comparison example, the polyacrylonitrile formulation described in b) was coated onto a polyester fabric and reused as a single-layer membrane for the glucose test according to German Patent Specification 3,922,495.

In comparison to the analogous sandwich system, the applied blood was distributed significantly more poorly on the application side, such that the opposite reagent side was also non-uniformly colored blue. Even after a relatively long period of action, the predominant part of the amount of sample applied was still on the application side.

EXAMPLE 2

Sandwich membrane with ascorbic acid protection in the macroporous application layer.

a) Polyethyleneimine-containing macroporous polymer blend membrane 1.04 g of polyethyleneimine (Polymin P ®. BASF) were also additionally added to the casting solution described in Example 1a. The membrane was prepared analogously to Example 1a).

b) Microporous, TMB-containing polyacrylonitrile membrane Preparation analogously to Example 1b on the fabric side of Example 2a)

The following impregnation solutions were impregnated into the polyethyleneimine-containing application layer in parallel experiments (hand doctor blade, 10 μm wet coating):
a) 0.25 per cent periodic acid solution in water
b) 0.25 per cent iodic acid in water and then dried using warm air.

The test was carried out using the following sample solutions to test with regard to ascorbic acid resistance:

| 1 | 2 | 3 | 4 | 5 | 6 | 7 | 8 | |
|---|---|---|---|---|---|---|---|---|
| 100 | 100 | 100 | 100 | 200 | 200 | 200 | 200 | mg/dl of glucose |
|  | 50 | 100 | 200 |  | 50 | 100 | 200 | mg/dl of ascorbic acid |

Results

With periodic acid impregnation

Very weak reactivity with sample solution 4 and reduced reactivity with sample solution 8. In all other cases the reactivity corresponded to the reference values 1 or 5. Comparison with commercial specimens showed that the prior art had thus been excelled.

With iodic acid impregnation

In all cases, even with the sample solutions 4 and 8, it was not possible to show virtually any reduced reactivity. Test strips with a complete ascorbic acid protection of this type were hitherto unknown.

EXAMPLE 3

Sandwich membrane with free carboxyl groups in the macroporous application layer.
a) Polyacrylic acid-containing macroporous polymer blend membrane 1.04 g of polyacrylic acid (63 per cent aqueous solution, Janssen-Chimica) were additionally also added to the casting solution described in Example 1a). The membrane was prepared analogously to Example 1a).
b) Microporous, TMB-containing polyacrylonitrile membrane The membrane was prepared analogously to Example 1b) on the fabric side of Example 3a).

EXAMPLE 4

Glucose detection by the hexokinase method
a) Macroporous polymer blend membrane The membrane was prepared in analogy to Example 1.
b) Microporous polyacrylonitrile membrane

| | |
|---|---|
| Dralon N (anionically modified polyacrylonitrile, Bayer AG) | 100.0 g |
| Dimethyl sulphoxide (DMSO) | 596.3 g |
| Titanium dioxides (RKB2, Bayer AG) | 156.4 g |
| Iodonitrotetrazolium chloride (INT) | 8.4 g |

Solution A 3.0 g of adenosine triphosphate (ATP, Behringwerke) 0.3 g of hexokinase (Genzyme 145 U/mg)
0.5 g of PIPES-buffer (Boehringer M.) and
0.5 g of magnesium acetate (Fluka) were dissolved in 15 ml of water and adjusted to pH 7 with NaOH Solution B 0.6 g of nicotinamide adenine dinucleotide (NAD, Sigma)
0.2 g of glucose-6-phosphate dehydrogenase (Genzyme, 333 U/mg)
0.6 g of diaphorase (Genzyme, 89.5 U/mg)
0.3 g of PIPES buffer and
0.3 g of BSA (bovine albumin, Fluka) were dissolved in 15 ml of water and adjusted to pH 7 with NaOH The impregnation solution A was impregnated into the side of the macroporous membrane in a layer thickness of 15 μm with the aid of a hand doctor blade and dried.

An analogous procedure was used with the impregnation solution B, which was incorporated, however, into the microporous side of the membrane containing the indicator.

In a parallel example, the impregnation solutions A and B were combined and coated onto the microporous reagent layer.

In both cases, a red color reaction which was unaffected by erythrocytes was obtained after application of whole blood to the opposite side. In the case of the parallel example, however, the reaction proceeded substantially more slowly and led to a less homogeneous discoloration.

What is claimed is:

1. A diagnostic test device for detecting the presence of an analyte in a fluid sample which device comprises a fluid permeable support member having a layer on one side thereof of a macroporous membrane comprising polyethyleneimine having impregnated therein iodate ion and on the other side of the support member having a layer of a microporous membrane having dispersed therein a chromogenic indicator which provides a colored response upon being oxidized.

2. The device of claim 1 wherein the macroporous membrane comprises a blend of polyethyleneimine, polyacrylonitrile, polyurethane and polyvinyl acetate and the microporous membrane is comprised of polyacrylonitrile.

3. The diagnostic device of claim 1 wherein the macroporous membrane contains pores greater than 0.2μ in diameter and the microporous membrane contains pores up to 0.2μ in diameter.

4. The diagnostic test device of claim 1 wherein iodic acid is the source of iodate ion.

5. A method for the detection of an analyte in a liquid sample suspected of containing ascorbate ion which comprises applying said liquid sample to the macroporous layer of the test device of claim 1.

6. The method of claim 5 wherein the analyte is glucose and the chromogenic indicator is 3,3',5,5'-tetramethyl benzidine.

* * * * *